(12) United States Patent
Hahn et al.

(10) Patent No.: US 11,699,530 B2
(45) Date of Patent: Jul. 11, 2023

(54) USE OF MULTIVARIATE ANALYSIS TO ASSESS TREATMENT APPROACHES

(71) Applicant: RENSSELAER POLYTECHNIC INSTITUTE, Troy, NY (US)

(72) Inventors: Juergen Hahn, Ballston Lake, NY (US); Troy Vargason, Troy, NY (US); Uwe Kruger, Ballston Lake, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 17/413,354

(22) PCT Filed: Dec. 11, 2019

(86) PCT No.: PCT/US2019/065642
§ 371 (c)(1),
(2) Date: Jun. 11, 2021

(87) PCT Pub. No.: WO2020/123604
PCT Pub. Date: Jun. 18, 2020

(65) Prior Publication Data
US 2022/0044823 A1    Feb. 10, 2022

Related U.S. Application Data

(60) Provisional application No. 62/945,921, filed on Dec. 10, 2019, provisional application No. 62/778,091, filed on Dec. 11, 2018.

(51) Int. Cl.
*G16H 50/30* (2018.01)
*G16H 10/60* (2018.01)

(52) U.S. Cl.
CPC ............ *G16H 50/30* (2018.01); *G16H 10/60* (2018.01)

(58) Field of Classification Search
CPC .............................. G16H 50/30; G16H 10/60
See application file for complete search history.

(56) References Cited

U.S. PATENT DOCUMENTS

| | | | |
|---|---|---|---|
| 5,827,600 A | 10/1998 | Ejiri et al. | |
| 6,642,690 B2 | 11/2003 | Kim | |
| 7,457,793 B2 | 11/2008 | Weigt et al. | |
| 8,388,530 B2 | 3/2013 | Shusterman | |
| 10,125,835 B2 | 11/2018 | Oshio et al. | |
| 2006/0040003 A1 | 2/2006 | Needleman et al. | |
| 2012/0296090 A1 | 11/2012 | Wong et al. | |
| 2017/0068795 A1 | 3/2017 | Liu et al. | |

FOREIGN PATENT DOCUMENTS

WO    2014193999 A2    12/2014

OTHER PUBLICATIONS

International Search Report and The Written Opinion of the International Searching Authority, International Application No. PCT/US2019/065642, dated Mar. 4, 2020.
Howsmon, D.P., et al., "Classification and adaptive behavior prediction of children with autism spectrum disorder based upon multivariate data analysis of markers of oxidative stress and DNA methylation," PLoS Computational Biology, vol. 13, No. 3, pp. 1-15, Mar. 16, 2017.
Vargason, T., et al., "Investigating Plasma Amino Acids for Differentiating Individuals with Autism Spectrum Disorder and Typically Developing Peers," Research in Autism Spectrum Disorders, vol. 50, pp. 60-72, Mar. 2018.
Vargason, T., et al., "Comparison of Three Clinical Trial Treatments for Autism Spectrum Disorder Through Multivariate Analysis of Changes in Metabolic Profiles and Adaptive Behavior," Frontiers in Cellular Neuroscience, vol. 12, Dec. 19, 2018.

*Primary Examiner* — Jerry Lin
(74) *Attorney, Agent, or Firm* — Murtha Cullina LLP; Anthony P. Gangemi

(57) ABSTRACT

Fisher discriminant analysis is performed on data sets of typically developing (TD) individuals and data sets of autism spectrum disorder (ASD) individuals to produce a model that classifies TD individuals from ASD individuals. The ASD data sets include pre-treatment folate-dependent one-carbon metabolism (FOCM) and transsulfuration (TS) pathway metabolic profile data and post-treatment folate-dependent one-carbon metabolism (FOCM) and transsulfuration (TS) pathway metabolic profile data for patients receiving one or more ASD treatments. Changes in adaptive behavior are predicted by utilizing regression of changes in adaptive behavior and changes in biochemical measurements observed in the data sets. Thus, the system can be used to predict the effectiveness of a given course of treatment for an ASD patient based on measured metabolite data of that patient, or to predict the overall effectiveness of a clinical trial based on metabolite data for the trial participants.

9 Claims, 8 Drawing Sheets

USE OF MULTIVARIATE ANALYSIS TO ASSESS TREATMENT APPROACHES

CROSS REFERENCE TO RELATED APPLICATION(S)

This application is a national stage filing of International Application No. PCT/US2019/065642, filed Dec. 11, 2019, which claims the benefit of U.S. Provisional Application Nos. 62/778,091, filed Dec. 11, 2018, and 62/945,921, filed Dec. 10, 2019, which are incorporated by reference as if disclosed herein in their entirety.

BACKGROUND

Deficits in communication and behavior are defining characteristics of autism spectrum disorder (ASD), a neurodevelopmental disorder estimated by the Centers for Disease Control and Prevention to affect 1 out of 59 children in the United States. The national economic burden of ASD in 2015 was calculated to be $268 billion, similar to the costs of diabetes and attention deficit hyperactivity disorder. ASD is a highly heterogeneous disorder in terms of how it presents itself in each individual, with as many as 95% of diagnosed children also affected by at least one co-occurring condition and regressive forms of the disorder not being uncommon. Despite the large body of research investigating the etiology of ASD, there is relatively limited understanding of the pathophysiology of the disorder aside from complex interactions between genetic and environmental contributors being involved.

As a result of the heterogeneity and lack of biological understanding of ASD, the current standards for diagnosis are clinical evaluations of patient behavior, which while comprehensive do not offer the objective assessment of ASD status that a biomarker can offer. A consequence of this gap in knowledge is initial ASD diagnoses being made at a median age of four years even though stable diagnoses have been shown to be possible at two years of age in a large percentage of children. Given that earlier behavioral intervention typically leads to milder ASD-related symptoms and improved development of social and behavioral skills later in life, it is of great interest to achieve improved methods of ASD screening. Identification of biological markers for diagnosing ASD or assessing ASD risk status would thus represent a significant step towards improving long-term outcomes in individuals with ASD.

Potential biomarkers for ASD diagnosis may involve the folate-dependent one-carbon metabolism (FOCM) and transsulfuration (TS) pathways as these pathways have been linked to metabolic abnormalities in ASD in several studies. Case-control studies show that markers of DNA methylation and intracellular redox status are significantly different in individuals with ASD compared to typically developing (TD) peers, suggesting perturbations both in the epigenetic control of gene expression and in the control of intracellular oxidative stress. Subsequent studies have found a strong ability to classify individuals as having ASD or being TD, as well as predict adaptive behavior, based on these measurements. Development of a mathematical model of these pathways with parameters estimated from clinical data has also pointed to several metabolic reactions that may be disrupted in individuals with ASD.

Aside from investigating FOCM/TS metabolites for diagnostic purposes, correcting activity in the FOCM and TS pathways may affect underlying biological processes that contribute to ASD pathophysiology, thus making metabolic abnormalities in these pathways promising targets for clinical treatment. Further, it has been suggested that early detection of metabolic dysfunction to determine ASD risk and allowing for proactive treatment strategies could potentially lead to practical intervention plans for at least a subset of those at risk for ASD. Since the aim of treatment, however, is not just to correct metabolic abnormalities, but also to alleviate the primary behavioral symptoms of ASD, it would be of great value to determine treatment targets where improvements in metabolic activity give rise to amelioration of observed behavior. Previous studies by the authors have investigated the effects of treatment with methylcobalamin (MeCbl) in combination with low-dose folinic acid (LDFA), tetrahydrobiopterin ($BH_4$), and high-dose folinic acid (HDFA) for improving metabolic and behavioral outcomes in individuals with ASD. The growing body of literature describing the efficacy of these treatments suggests unique mechanisms by which each acts upon metabolic pathways that may be dysfunctional in ASD.

MeCbl, one treatment option for ASD that has been explored, is a cofactor for the methionine synthase enzyme that contributes to the process of DNA methylation. Levels of methionine synthase messenger RNA in the frontal cortex typically decrease with age, but this decrease has been found to occur more quickly in ASD even though actual levels of the enzyme do not appear to be affected significantly. Concentrations of MeCbl in the frontal cortex of children with ASD have been measured to be three times lower than those in TD children, with an associated three-fold decrease in methionine synthase activity also measured. It has been suggested that cobalamin transporter polymorphisms and mutations may contribute to the development of ASD. Open-label and double-blind placebo-controlled studies of MeCbl treatment have observed improvement in metabolism and ASD-related symptoms in children with the disorder.

Another studied treatment for ASD involves $BH_4$, which has diverse roles in monoamine neurotransmitter production, phenylalanine breakdown, and nitric oxide synthesis. Reduced cerebrospinal fluid levels of $BH_4$ have been reported in children with ASD, with one study reporting these levels to be 42% of those found in TD children and a small open-label trial of $BH_4$ requiring deficient levels as an inclusion criterion. Analysis of genes related to $BH_4$ pathways has suggested that the synthesis of $BH_4$ may be impaired in individuals with ASD. One double-blind placebo-controlled study with $BH_4$ observed increases in social interaction after six months of treatment, while a more recent trial described significant improvements in ASD-related mannerisms, hyperactivity, inappropriate speech, and social awareness. Although it is unclear which underlying biological mechanisms are targeted by $BH_4$ treatment, its therapeutic effect may derive from its correction of oxidative stress and overall folate metabolism in the central nervous system.

Folinic acid is also a potential treatment for ASD and is a naturally-occurring form of folate, which is included in purine and pyrimidine productions, aids in the transfer of carbon during the process of amino acid synthesis, and contributes to DNA methylation processes. Early studies of folate deficiency in the central nervous system indicated a potential connection to cases of ASD and other neurological deficits, with later studies also reporting increased levels of folate receptor autoantibodies in the blood to be correlated with the presentation of ASD-related symptoms and physiology. Additionally, higher rates of developmental deficits and ASD-like behaviors have been observed in animal models administered folate receptor antibodies during gestation and the pre-weaning period. The use of folate supplements during pregnancy may serve to combat these deleterious effects as it has been associated with a reduced risk of ASD in the child; this is likely due to folate's protective effect for proper neural tube development. Treatment with folinic acid has also been found to correct certain abnormalities of the cerebrospinal fluid and improve ASD-related symptoms and behavior.

Even though a number of studies have tested the effect of treatment on individually measured compounds or on certain behavioral measures in individuals with ASD, there remains a need to study the effect of a treatment on combinations of metabolites of the FOCM/TS pathways and to correlate pathway-wide changes to shifts in behavioral measures.

SUMMARY

Accordingly, the present disclosure relates to methods and systems for assessing, comparing, and/or predicting the effectiveness of treatments for disorders using multivariate statistical analysis. In one embodiment, the method includes the steps of developing multivariate models of the effects of treatments on a condition and then using a regression analysis to predict changes in the condition as a result of changes in the treatment. In some embodiments, the system includes at least one processor and a non-transitory computer storage media encoded with one or more computer programs executed by the at least one processor. In some embodiments, the one or more computer programs are configured to perform a multivariate statistical analysis on one or more data sets of typically developing (TD) individuals and one or more data sets of autism spectrum disorder (ASD) individuals to produce a model that classifies TD individuals from ASD individuals, wherein the TD data sets include metabolic profile data for a plurality of TD individuals and ASD data sets include pre-treatment metabolic profile data and post-treatment metabolic profile data for patients receiving one or more ASD treatments; calculate pre-treatment discriminant scores and post-treatment discriminant scores for a plurality of patients in the ASD data sets; identify a change from the pre-treatment discriminant score to the post-treatment discriminant score to quantify a treatment effect on metabolic profiles of the plurality of patients; perform a treatment effect regression analysis on changes in adaptive behavior scores and the metabolic profiles of the plurality of patients; and quantify a predicted adaptive behavior score change for a target patient from a measured metabolic profile change in the target patient, wherein the target patient is undergoing at least one of the one or more ASD treatments. In some embodiments, the one or more computer programs configured to identify a change from the pre-treatment discriminant score to the post-treatment discriminant score to quantify a treatment effect on metabolic profiles of the plurality of patients is further configured to calculate, for the plurality of patients in the ASD data sets, a first probability that the model will classify a data set patient as TD pre-treatment and a second probability that the model will classify the data set patient as TD post-treatment; and identify a change from the first probability to the second probability. In some embodiments, an increase in probability from the first probability to the second probability identifies a positive treatment effect.

In some embodiments, the metabolic profile data includes data for folate-dependent one-carbon metabolism (FOCM) metabolites, transsulfuration (TS) pathway metabolites, methionine, SAM, SAH, SAM/SAH, 8-OHG, adenosine, homocysteine, cysteine, γ-L-glutamyl-L-cysteine (Glu.-Cys.), L-cysteine-L-glycine (Cys.-Gly.), tGSH, fGSH, GSSG, fGSH/GSSG, tGSH/GSSG, chlorotyrosine, nitrotyrosine, tyrosine, tryptophane, fCystine, fCysteine, fCystine/fCysteine, a percent of DNA methylation, a percent of oxidized glutathione, or combinations thereof. In some embodiments, the multivariate statistical analysis includes performing a Fisher discriminant analysis. In some embodiments, the one or more ASD treatments include MeCbl+ LDFA, $BH_4$, HDFA, or combinations thereof. In some embodiments, the one or more ASD treatments include placebo treatments. In some embodiments, the adaptive behavior score includes a Vineland Adaptive Behavior Scales (VABS) Composite score. In some embodiments, the treatment effect regression analysis includes use of a kernel partial least squares algorithm.

Some embodiments of the present disclosure include a computer implemented method to predict changes in adaptive behavior including performing a multivariate statistical analysis on one or more data sets of TD individuals and one or more data sets of ASD individuals to produce a model that classifies TD individuals from ASD individuals, wherein the TD data sets include metabolic profile data for a plurality of TD individuals and ASD data sets include pre-treatment metabolic profile data and post-treatment metabolic profile data for patients receiving one or more ASD treatments; calculating pre-treatment discriminant scores and post-treatment discriminant scores for a plurality of patients in the ASD data sets; identifying a change from the pre-treatment discriminant score to the post-treatment discriminant score to quantify a treatment effect on metabolic profiles of the plurality of patients; performing a treatment effect regression analysis on changes in adaptive behavior scores and metabolic profiles of the plurality of patients; and quantifying a predicted adaptive behavior score change for a target patient from a measured metabolic profile change in the target patient, wherein the target patient is undergoing at least one of the one or more ASD treatments.

Some embodiments of the present disclosure include a computer implemented method to predict changes in adaptive behavior including performing Fisher discriminant analysis on one or more data sets of TD individuals and one or more data sets of ASD individuals to produce a model that classifies TD individuals from ASD individuals, wherein the TD data sets include FOCM and TS pathway metabolic profile data for a plurality of TD individuals and ASD data sets include pre-treatment FOCM and TS pathway metabolic profile data and post-treatment FOCM and TS pathway metabolic profile data for patients receiving one or more ASD treatments; calculating, for the plurality of patients in the ASD data sets, a first probability that the model will classify a data set patient as TD pre-treatment and a second probability that the model will classify the data set patient as TD post-treatment; identifying a change from the first probability to the second probability to quantify a treatment effect on metabolic profiles of the plurality of patients; performing a treatment effect regression analysis on changes in adaptive behavior scores and metabolic profiles of the plurality of patients; and quantifying a predicted adaptive behavior score change for a target patient from a measured metabolic profile change in the target patient, wherein the target patient is undergoing at least one of the one or more ASD treatments.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein.

DETAILED DESCRIPTION

Figure 1:
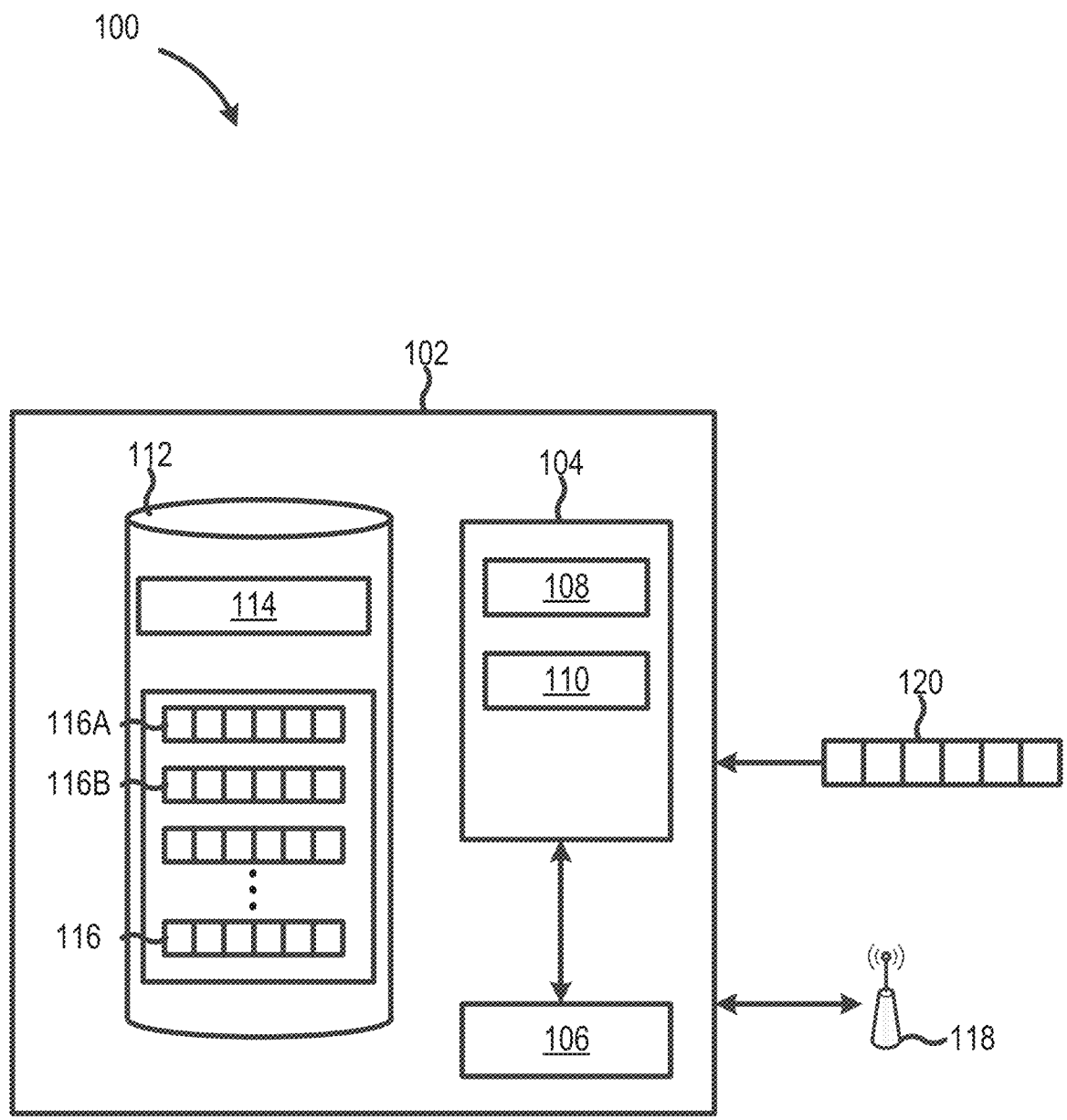
FIG. 1 is schematic drawing of a system for predicting changes in adaptive behavior according to some embodiments of the present disclosure.

Referring now to FIG. 1, some embodiments of the present disclosure are directed to a system 100 to predict changes in adaptive behavior. The system 100 includes a non-transitory computer storage media 102 encoded with one or more computer programs 104 executed by at least one processor 106.

In some embodiments, non-transitory computer storage media 102 includes a classifier 108. In some embodiments, classifier 108 can be any script, file, program, application, set of instructions, or computer-executable code, that is configured to enable a computing device on which the classifier 108 is executed to classify incoming data sets into one of a typically developing (TD) class and autism spectrum disorder (ASD) class.

In some embodiments, non-transitory computer storage media 102 includes a scoring engine 110. In some embodiments, system 100 includes a memory 112. In some embodiments, system 100 includes class templates 114 and data sets 116. In some embodiments, class templates 114 and data sets 116 are stored on the memory 112. In some embodiments, memory 112 is local, remote, or combinations thereof. In some embodiments, system 100 includes a communication module 118 configured to send and receive communications, data, etc. In some embodiments, communication module 118 is configured to receive a test data set 120 and communicate the test data set to non-transitory computer storage media 102 (not pictured).

In some embodiments, classifier 108 generates class template 114 for data sets 116. In some embodiments, classifier 108 generates the class template 114 using Fisher Discriminant Analysis (FDA). FDA can maximize differences between multiple classes. In some embodiments, classifier 108, using FDA, determines a linear combination of the values in each of the data sets 116 that projects the data sets onto a line joining the mean of the ASD and TD groups. In some embodiments, classifier 108 calculates the linear combination such that the linear combination projects the data sets 116 associated with the same class near one another and data sets 116 associated with the other class disparately. For example, classifier 108 can calculate a linear combination that projects the data sets 116 into a TD class and an ASD class. In some embodiments, classifier 108 saves the linear combination as a class template 114. In some embodiments, classifier 108 also determines a threshold that separates the two classes.

In some embodiments, classifier 108 uses nonlinear techniques to classify data sets 116 into the ASD class and the TD class. For example, classifier 108 can use kernel partial least squares (KPLS) to classify the data sets. Kernel techniques provide general nonlinear extensions to the popular linear partial least squares (PLS) regression. The KPLS algorithm commences by defining a nonlinear transformation $f=\psi(x)$ on the predictor set x. In some embodiments, $\psi(x)$ is a Guassian kernel. In some embodiments, rather than regress x as a linear PLS, y can be regressed onto the higher dimensional feature space f.

As discussed above, in some embodiments, classifier 108 generates class templates 114 based on training data that includes data sets 116 from both ASD and TD patients. In some embodiments, data sets 116 (and the incoming test data set 120) are each a vector that includes a plurality of values. In some embodiments, a plurality of the values represents a metabolite concentration. In some embodiments, the metabolite concentrations stored in the data sets 116 are the concentration of at least one of folate-dependent one-carbon metabolism (FOCM) metabolites, transsulfuration (TS) pathway metabolites, methionine, SAM, SAH, SAM/SAH, 8-OHG, adenosine, homocysteine, cysteine, γ-L-glutamyl-L-cysteine (Glu.-Cys.), L-cysteine-L-glycine (Cys.-Gly.), tGSH, fGSH, GSSG, fGSH/GSSG, tGSH/GSSG, chlorotyrosine, nitrotyrosine, tyrosine, tryptophane, fCystine, fCysteine, fCystine/fCysteine, a percent of DNA methylation, a percent of oxidized glutathione, or combinations thereof. In some embodiments, data sets 116 includes a value for each of the above metabolites. In some embodiments, data sets 116 can include a value for a sub-population of the metabolites. In some embodiments, the order of the metabolite concentrations are arranged in the same order in each of the data sets 116. In some embodiments, test data set 120 includes a value for each metabolite in data sets 116. In some embodiments, test data set 120 includes a value for substantially all metabolites in data sets 116.

As discussed above, in some embodiments, non-transitory computer storage media 102 includes the scoring engine 110. In some embodiments, scoring engine 110 is any script, file, program, application, set of instructions, or computer-executable code, that is configured to enable a computing device on which the scoring engine 106 is executed to convert a data set into a score, which is used as a biomarker to categorize the data set, e.g., data set 116 and/or test data set 120, into a TD class or ASD class. In some embodiments, upon receiving test data set 120, scoring engine 110 retrieves class template 114 from the memory 112 and calculates a score for test data set 120 based on the linear combination stored in the class template 114. In some embodiments, scoring engine 110 compares the calculated score to the threshold to determine if the test data set 120 should be associated with the TD class or the ASD class.

In some embodiments, as discussed above, non-transitory computer storage media 102 is encoded with one or more computer programs 104 executed by at least one processor 106. In some embodiments, one or more computer programs 104 are configured to perform a multivariate statistical analysis on one or more data sets of ASD individuals 116A and one or more data sets of TD individuals 116B and to produce a model, e.g., classifier 108, that classifies TD individuals from ASD individuals. As discussed above, in some embodiments, the multivariate statistical analysis includes performing a Fisher discriminant analysis. In some embodiments, TD data sets 116B include metabolic profile data for a plurality of TD individuals and ASD data sets 116A include pre-treatment metabolic profile data and post-treatment metabolic profile data for patients receiving one or more ASD treatments. In some embodiments, the one or more ASD treatments include any treatments whose effect is to adjust local or systemic levels of a given metabolite in a target patient. In some embodiments, the one or more ASD treatments include administration of MeCbl+LDFA, $BH_4$, HDFA, or combinations thereof. In some embodiments, the one or more ASD treatments further include placebo treatments. As discussed above, in some embodiments, the metabolic profile data includes data for FOCM metabolites, TS pathway metabolites, methionine, SAM, SAH, SAM/SAH, 8-OHG, adenosine, homocysteine, cysteine, γ-L-glutamyl-L-cysteine (Glu.-Cys.), L-cysteine-L-glycine (Cys.-Gly.), tGSH, fGSH, GSSG, fGSH/GSSG, tGSH/GSSG, chlorotyrosine, nitrotyrosine, tyrosine, tryptophane, fCystine, fCysteine, fCystine/fCysteine, a percent of DNA methylation, a percent of oxidized glutathione, or combinations thereof.

In some embodiments, one or more computer programs 104 are configured to calculate pre-treatment discriminant scores and post-treatment discriminant scores for a plurality of patients in ASD data sets 116A. e.g., via scoring engine 110. In some embodiments, one or more computer programs 104 are configured to identify a change from the pre-treatment discriminant score to the post-treatment discriminant score to quantify a treatment effect on metabolic profiles of the plurality of patients. In some embodiments, one or more computer programs 104 are configured to calculate a probability distribution function (PDF) of the pre-treatment discriminant scores and the post-treatment discriminant scores. In some embodiments, one or more computer programs 104 are configured to calculate, for the plurality of patients in the ASD data sets, a first probability that the model will classify a data set patient as TD pre-treatment and a second probability that the model will classify the data set patient as TD post-treatment. In some embodiments, one or more computer programs 104 are configured to identify a change from the first probability to the second probability. The null hypothesis, $H_0$, for classification states that a participant belongs to the TD group. With this hypothesis, the Type I (false positive) error is the probability of incorrectly classifying a TD individual as having ASD. The Type II (false negative) error is then the probability of incorrectly classifying a participant with ASD as being TD. In some embodiments, the change in Type II error yielded by a certain treatment, e.g., increased probability of being classified as a TD individual after treatment, was used to quantify the abilities of these treatments to shift the metabolic profiles of individuals with ASD to be more, or less, similar to those of the TD class, thus quantifying a treatment effect on metabolic profiles of the plurality of patients. As will be discussed in greater detail below, through evaluation of the FDA model on the clinical trial data sets, the MeCbl+LDFA treatment was found to provide the greatest correction in ASD-related metabolic abnormalities, with the effects of $BH_4$ just slightly smaller; both of these treatments increased the rate of ASD misclassification by more than 40% each.

In some embodiments, one or more computer programs 104 are configured to perform a treatment effect regression analysis on changes in adaptive behavior scores and the metabolic profiles of the plurality of patients. In some embodiments, the treatment effect regression analysis includes use of a kernel partial least squares algorithm. As a result, one or more computer programs 104 are configured to predict an adaptive behavior score change for a target patient undergoing at least one of the one or more ASD treatments, e.g., that of test data set 120, from a measured metabolic profile change in the target patient. In some embodiments, the adaptive behavior score includes a Vineland Adaptive Behavior Scales (VABS) Composite score. In some embodiments, one or more computer programs 104 are configured to quantify and/or output the predicted adaptive behavior score change.

In some embodiments, system 100 is used to predict the effectiveness of a given course of treatment for an ASD patient based on measured metabolite data of that patient. In some embodiments, system 100 is used to predict the overall effectiveness of a clinical trial based on metabolite data for the trial participants.

Additional background and supporting disclosure concerning the multivariate statistical analysis of the present disclosure can be found in Howsmon, D. P., Kruger, U., Melnyk, S., James, S. J., and Hahn, J. (2017). "Classification and adaptive behavior prediction of children with autism spectrum disorder based upon multivariate data analysis of markers of oxidative stress and DNA methylation." PLOS Comput. Biol. 13, e1005385, and US/2018/0358127, each of which are incorporated herein by reference in their entireties.

Figure 2A:
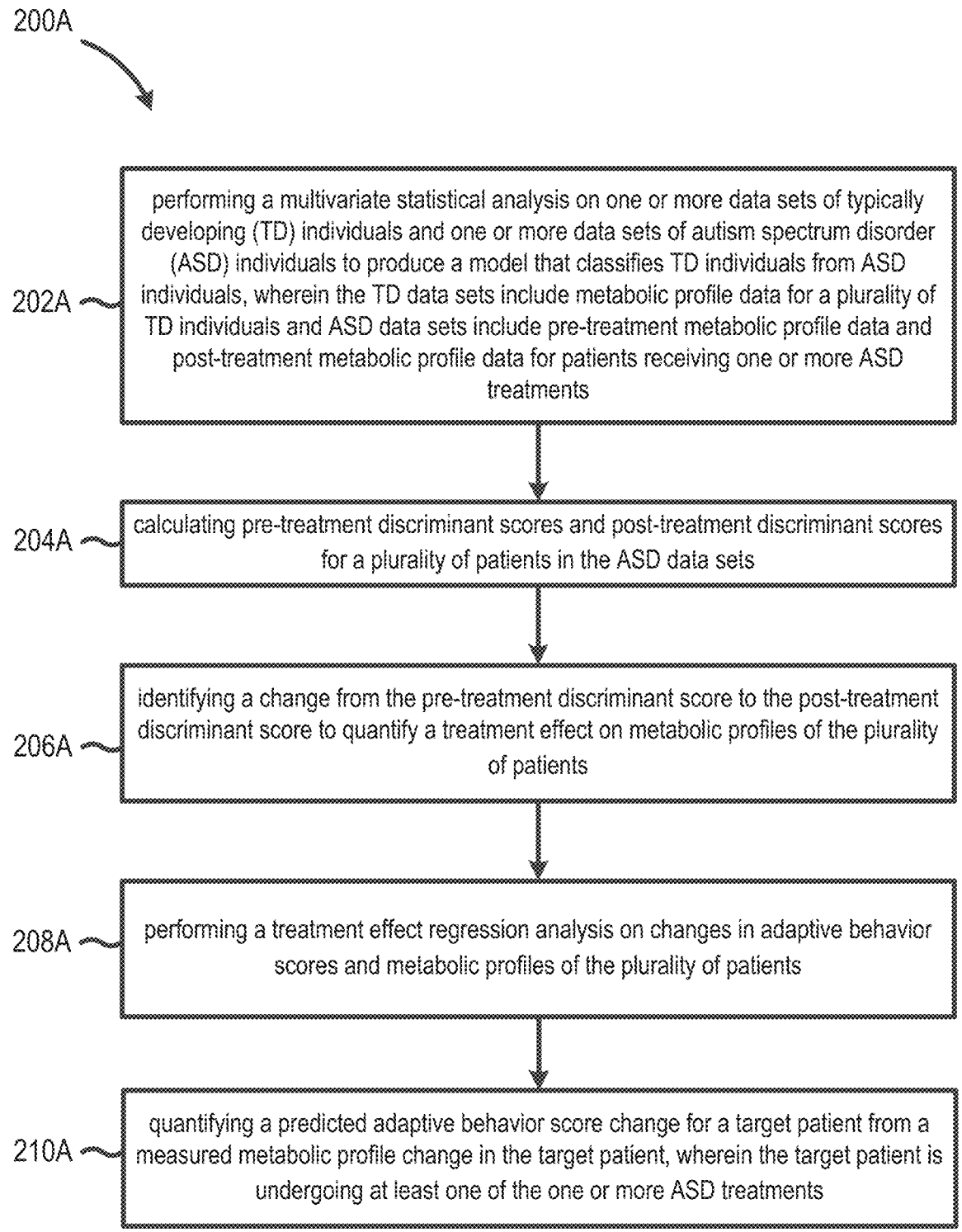
FIG. 2A is a chart of a method for predicting changes in adaptive behavior according to some embodiments of the present disclosure.

Referring now to FIG. 2A, some embodiments of the present disclosure are directed to a computer implemented method 200A for predicting changes in adaptive behavior. At 202A, a multivariate statistical analysis is performed on one or more data sets of TD individuals and one or more data sets of ASD individuals to produce a model that classifies TD individuals from ASD individuals. As discussed above, in some embodiments, the TD data sets include metabolic profile data for a plurality of TD individuals. In some embodiments, the ASD data sets include pre-treatment metabolic profile data and post-treatment metabolic profile data for patients receiving one or more ASD treatments. In some embodiments, the metabolic profile data includes data for FOCM metabolites, TS pathway metabolites, methionine, SAM, SAH, SAM/SAH, 8-OHG, adenosine, homocysteine, cysteine, γ-L-glutamyl-L-cysteine (Glu.-Cys.), L-cysteine-L-glycine (Cys.-Gly.), tGSH, fGSH, GSSG, fGSH/GSSG, tGSH/GSSG, chlorotyrosine, nitrotyrosine, tyrosine, tryptophane, fCystine, fCysteine, fCystine/fCysteine, a percent of DNA methylation, a percent of oxidized glutathione, or combinations thereof. In some embodiments, the multivariate statistical analysis comprises performing a Fisher discriminant analysis. In some embodiments, the one or more ASD treatments include MeCbl+LDFA, $BH_4$, HDFA, or combinations thereof. In some embodiments, the one or more ASD treatments include placebo treatments.

At 204A, pre-treatment discriminant scores and post-treatment discriminant scores are calculated for a plurality of patients in the ASD data sets. At 206A, a change from the pre-treatment discriminant score to the post-treatment discriminant score is identified to quantify a treatment effect on metabolic profiles of the plurality of patients. In some embodiments, identifying step 206A includes calculating, for the plurality of patients in the ASD data sets, a first probability that the model will classify a data set patient as TD pre-treatment and a second probability that the model will classify the data set patient as TD post-treatment, and identifying a change from the first probability to the second probability. As discussed above, and without wishing to be bound by theory, an increase in probability from the first probability to the second probability identifies a positive treatment effect.

At 208A, a treatment effect regression analysis on changes in adaptive behavior scores and metabolic profiles of the plurality of patients is performed. As discussed above, in some embodiments, the adaptive behavior score includes a Vineland Adaptive Behavior Scales (VABS) Composite score. In some embodiments, the treatment effect regression analysis includes use of a kernel partial least squares algorithm. At 210A, a predicted adaptive behavior score change is quantified for a target patient from a measured metabolic profile change in the target patient who is undergoing at least one of the one or more ASD treatments.

Figure 2B:
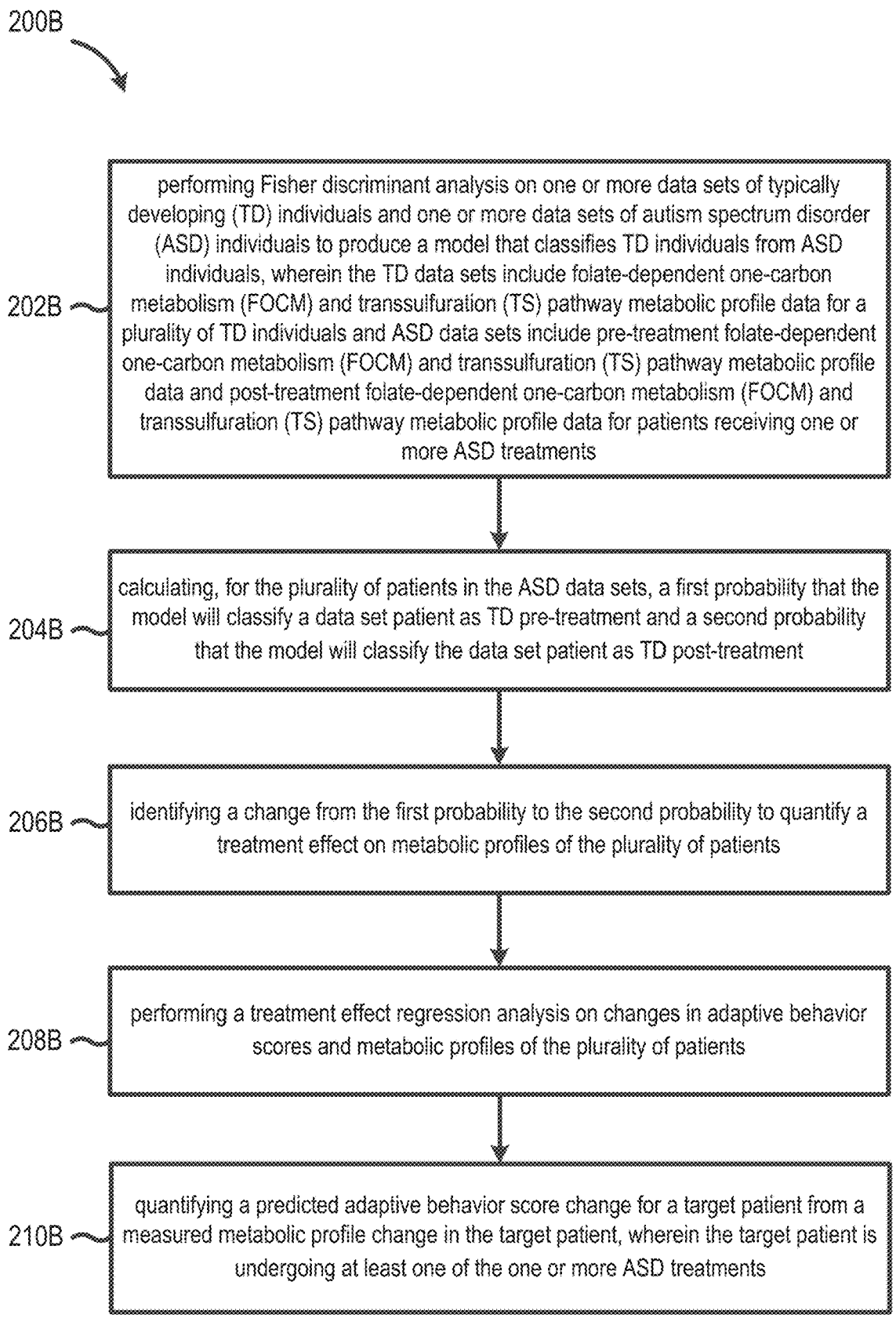
FIG. 2B is a chart of a method for predicting changes in adaptive behavior according to some embodiments of the present disclosure.

Referring now to FIG. 2B, some embodiments of the present disclosure are directed to a computer implemented method 200B to predict changes in adaptive behavior. At 202B, Fisher discriminant analysis is performed on one or more data sets of TD individuals and one or more data sets of ASD individuals to produce a model that classifies TD individuals from ASD individuals, wherein the TD data sets include FOCM) and TS pathway metabolic profile data for a plurality of TD individuals and ASD data sets include pre-treatment FOCM and TS pathway metabolic profile data and post-treatment FOCM and TS pathway metabolic profile data for patients receiving one or more ASD treatments. At 204B, a first probability that the model will classify a data set patient as TD pre-treatment and a second probability that the model will classify the data set patient as TD post-treatment are calculated for the plurality of patients in the ASD data sets. At 206B, a change from the first probability to the second probability is identified to quantify a treatment effect on metabolic profiles of the plurality of patients. At 208B, a treatment effect regression analysis is performed on changes in adaptive behavior scores and metabolic profiles of the plurality of patients. At 210B, a predicted adaptive behavior score change is quantified for a target patient from a measured metabolic profile change in the target patient, wherein the target patient is undergoing at least one of the one or more ASD treatments.

EXAMPLES

Description of Data Sets. Four data sets describing plasma FOCM/TS measurements from previous separately investigated and published studies were obtained. The recommendations of the respective Institutional Review Boards (IRBs) described below were followed, with study protocols also approved by the respective IRBs. Written informed consent was provided by parents of study participants and assent was given by participants themselves, when appropriate, in accordance with the Declaration of Helsinki.

Case-Control Data. Case-control data from the Integrated Metabolic and Genomic Endeavor (IMAGE) study at Arkansas Children's Research Institute was also used. The case-control group consisted of children between 3 and 10 years of age with a diagnosis of autistic disorder according to the Diagnostic and Statistical Manual of Mental Disorders, Fourth Edition (DSM-IV), the Autism Diagnostic Observation Schedule, and/or the Childhood Autism Ratings Scales (score greater than 30). TD controls were age-matched and had no indications of behavioral or neurological disorders as reported by their parents. In the ASD cohort, 85% of participants were male while 48% of the TD cohort were male. The protocol for this study was approved by the IRB at the University of Arkansas for Medical Sciences in Little Rock, Ark.

MeCbl+LDFA Treatment Data. Subcutaneously injected MeCbl (75 µg/kg, once every three days) in combination with oral LDFA (400 µg, twice per day) was given to children with autism in a 12-week open-label trial. Included children were aged 2 to 7 years and met the diagnostic criteria for autism as defined by the DSM-IV in addition to having a Childhood Autism Rating Scales score greater than 30. Boys and girls made up 82% and 18% of participants in this study, respectively. The IRB at the University of Arkansas for Medical Sciences approved the protocol for this study.

$BH_4$ Treatment Data. A 16-week open-label trial investigated the effects of orally administered $BH_4$ (20 mg/kg, once per day) in children aged 2 to 6 years old with a previous diagnosis of ASD that was confirmed at the time of evaluation with DSM-IV criteria. Included children also needed to exhibit social or language delays and have normal concentrations of $BH_4$ in their cerebrospinal fluid. Study participants were 90% males. Approval for this study was given by the IRB at the University of Texas Health Science Center at Houston, Tex. FOCM/TS markers were measured at 8 and 16 weeks following the onset of treatment in this trial; to maintain consistency with the other trials where markers were measured after 12 weeks, the averages of the measurements taken at 8 and 16 weeks were used.

HDFA Treatment Data. A double-blind placebo-controlled trial of HDFA (2 mg/kg per day up to a maximum of 50 mg daily, given orally) was administered over 12 weeks to children between 3 and 14 years of age. ASD diagnoses were made using the Autism Diagnostic Observation Schedule and/or Autism Diagnostic Interview—Revised, or by agreement between physician, psychologist, and speech therapist, or by a physician's diagnosis according to the Diagnostic and Statistical Manual of Mental Disorders, Fifth Edition with later confirmation by the investigators. All children were required to have documented language impairment. 78% of the treatment group were male while 80% of the placebo group were male. The protocol was approved by the IRB at the University of Arkansas for Medical Sciences. All data for participants receiving a placebo in the current analysis were provided.

Biochemical Measurements. Concentrations and ratios of metabolites in the FOCM and TS pathways were measured in each of the above studies, with fifteen measurements appearing in all four data sets. Six of these measures were associated with DNA methylation: methionine, S-adenosylmethionine (SAM), S-adenosylhomocysteine (SAH), the SAM/SAH ratio (an indicator of DNA methylation capacity), homocysteine, and adenosine. The remaining nine measures were precursors of glutathione or markers of redox metabolism: total cysteine, glutamylcysteine (Glu-Cys), cysteinylglycine (Cys-Gly), total and free reduced glutathione (tGSH and fGSH, respectively), oxidized glutathione (GSSG), the ratios of total and free reduced glutathione to oxidized glutathione (tGSH/GSSG and fGSH/GSSG, respectively; these are indicators of intracellular oxidative stress), and percent oxidized glutathione (a derived measure calculated as $2GSSG/[GSH+2GSSG]$).

Adaptive Behavior Assessment. The Vineland Adaptive Behavior scales (VABS) were used in all of the above studies to measure adaptive behavior in the communication, daily living, and social subdomains. The VABS Composite score incorporates these subdomains to provide a single measure of adaptive behavior. Higher scores indicate better development of adaptive behavior.

Inclusion Criteria. Participants of the IMAGE study were included in the current analysis if they had a complete panel of the fifteen FOCM/TS markers of interest. 92 participants with ASD and 82 TD controls met this criterion and were thus considered for further analysis. Participants of the clinical trials were included if they had complete pre- and post-treatment measurements for these fifteen markers in addition to pre- and post-treatment VABS Composite scores. Meeting these criteria were 33 participants receiving MeCbl+LDFA, 8 participants receiving BH$_4$, 14 participants receiving HDFA, and 19 participants receiving a placebo (74 participants with ASD in total), and summarized in Table 1 below.

TABLE 1

Participant numbers from the four data sets used

| Study | ASD Participants | TD Participants | Inclusion Criteria |
|---|---|---|---|
| IMAGE Case-l Contro | 92 | 82 | Complete panel of FOCM/TS |
| MeCbl + LDFA Trial | 33 | 0 | Complete pre- and treatment panel of FOCM/TS VABS Composite |
| BH$_4$ Trial | 8 | 0 | |
| HDFA Trial | 14 (+19 placebo) | 0 | |
| Placebo* | 19 | 0 | |

Multivariate Statistical Analysis. The analytical techniques employed by this embodiment were coded in MATLAB. All data used for model training were normalized such that each FOCM/TS marker had a mean of zero and a standard deviation of one across all training samples. Model validation samples were then normalized according to the mean/standard deviation parameters used for normalization of the training data.

Fisher Discriminant Analysis. Individuals of the IMAGE study were separated into ASD and TD cohorts using Fisher discriminant analysis (FDA). FDA used the data matrix X of size n×m as input, where n study participants are each defined by m biochemical measurements. Sample information for study participant i was contained in row vector $x_i$ (size 1×m) and that participant's value for measurement j is indicated by $x_{i,j}$. The input matrix X were considered as two matrices $X_{ASD}$ and $X_{TD}$ taken to represent the separate samples for the ASD and TD cohorts, respectively, with $X_{ASD}$ composed of $n_{ASD}$ samples and $X_{TD}$ having $n_{TD}$ samples. For the two-class problem presented here, FDA defined the between-class scatter matrix $S_B$ (size m×m) as $$S_B = n_{ASD}(\bar{x}_{ASD} - \bar{x})(\bar{x}_{ASD} - \bar{x})^T + n_{TD}(\bar{x}_{TD} - \bar{x})(\bar{x}_{TD} - \bar{x})^T$$

where $\bar{x}_{ASD}$ denotes the mean vector of samples in XASD, $\bar{x}_{TD}$ represents the mean vector among samples in $X_{TD}$, and $\bar{x}$ indicates the mean vector across all samples in X. The within-class scatter matrix $S_W$ (size m×m) was then defined as $$S_w = n_{ASD} \sum_{i=1}^{n_{ASD}} (x_i - \bar{x}_{ASD})(x_i - \bar{x}_{ASD})^T + n_{TD} \sum_{i=1}^{n_{TD}} (x_i - \bar{x}_{TD})(x_i - \bar{x}_{TD})^T$$

where $x_i$ represents an individual sample from either the ASD or TD cohort. Using this information, FDA determined the m×1 projection vector w that satisfies the objective function FDA determines the m×1 projection vector w that satisfies the objective function $$\max_w \frac{w^T S_B w}{w^T S_w w} \rightarrow Jw = S_w^{-1} S_B w$$

where the optimal solution is given by the eigenvector of the matrix product $S_W^{-1} S_B$. A final discriminant score $t_i$, which is the projection of the ith data point onto the projection vector w, was given by $$t_i = x_i \cdot w = x_{i,1} w_1 + x_{i,2} w_2 + \ldots + x_{i,m} w_m.$$

Kernel Density Estimation. Kernel density estimation assumed that samples not included in the estimation of a PDF will likely be near the reference samples that were used. As part of the estimation procedure, a Gaussian kernel function was centered on each reference sample; the sum of the kernel functions associated with the samples of a particular cohort was then taken to be representative of that cohort's total PDF.

Null Hypothesis for Classification. As discussed above, the null hypothesis, $H_0$, for classification states that a participant belongs to the TD group. With this hypothesis, the Type I (false positive) error is the probability of incorrectly classifying a TD participant as having ASD. The Type II (false negative) error is then the probability of incorrectly classifying a participant with ASD as being TD. These errors' magnitudes are dictated by the choice of the discriminant score threshold for $H_0$ and the amount of overlap between the PDFs for the two cohorts. In order to balance the Type I and Type II errors, this analysis placed the threshold $H_0$ at the point where the absolute difference between these errors in the fitted model was minimized.

Figure 3A:
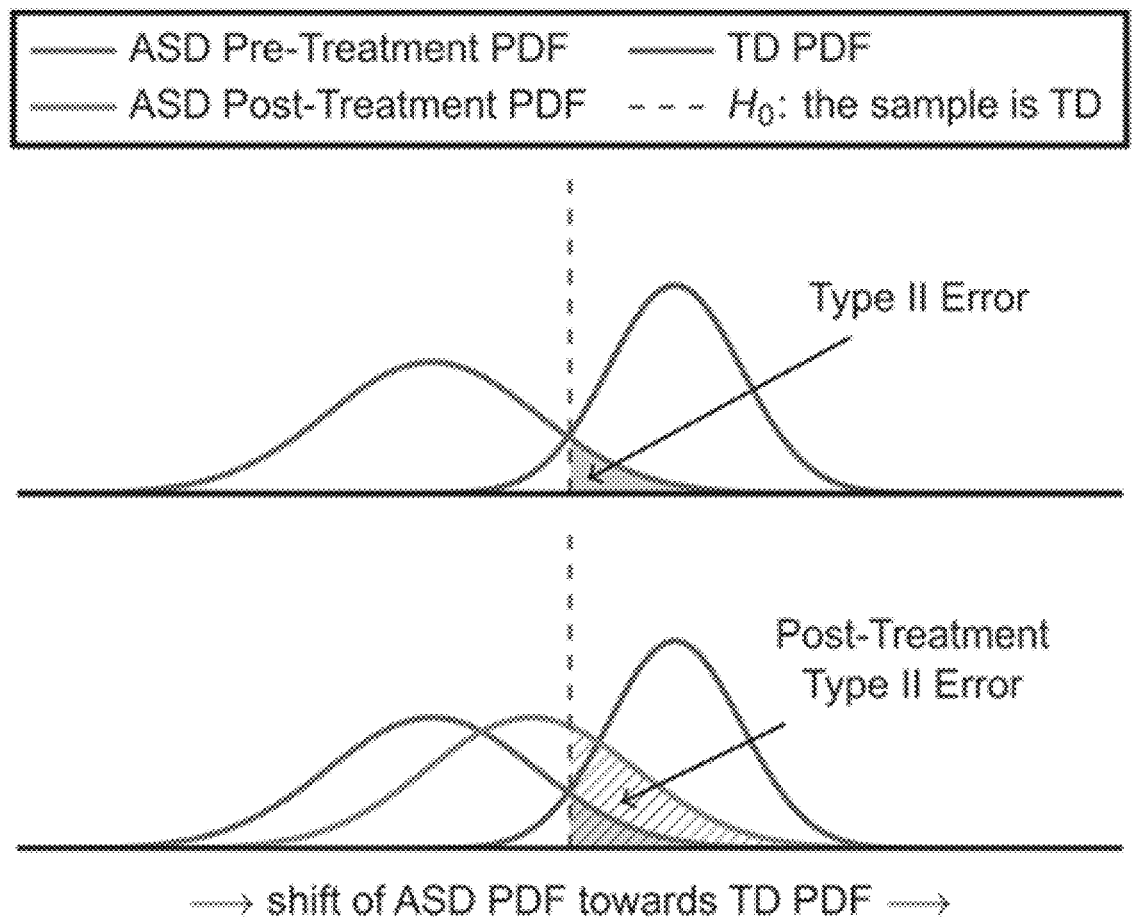
FIG. 3A is a graph of classification results for a Fisher Discriminant Analysis model according to some embodiments of the present disclosure.
Figure 3B:
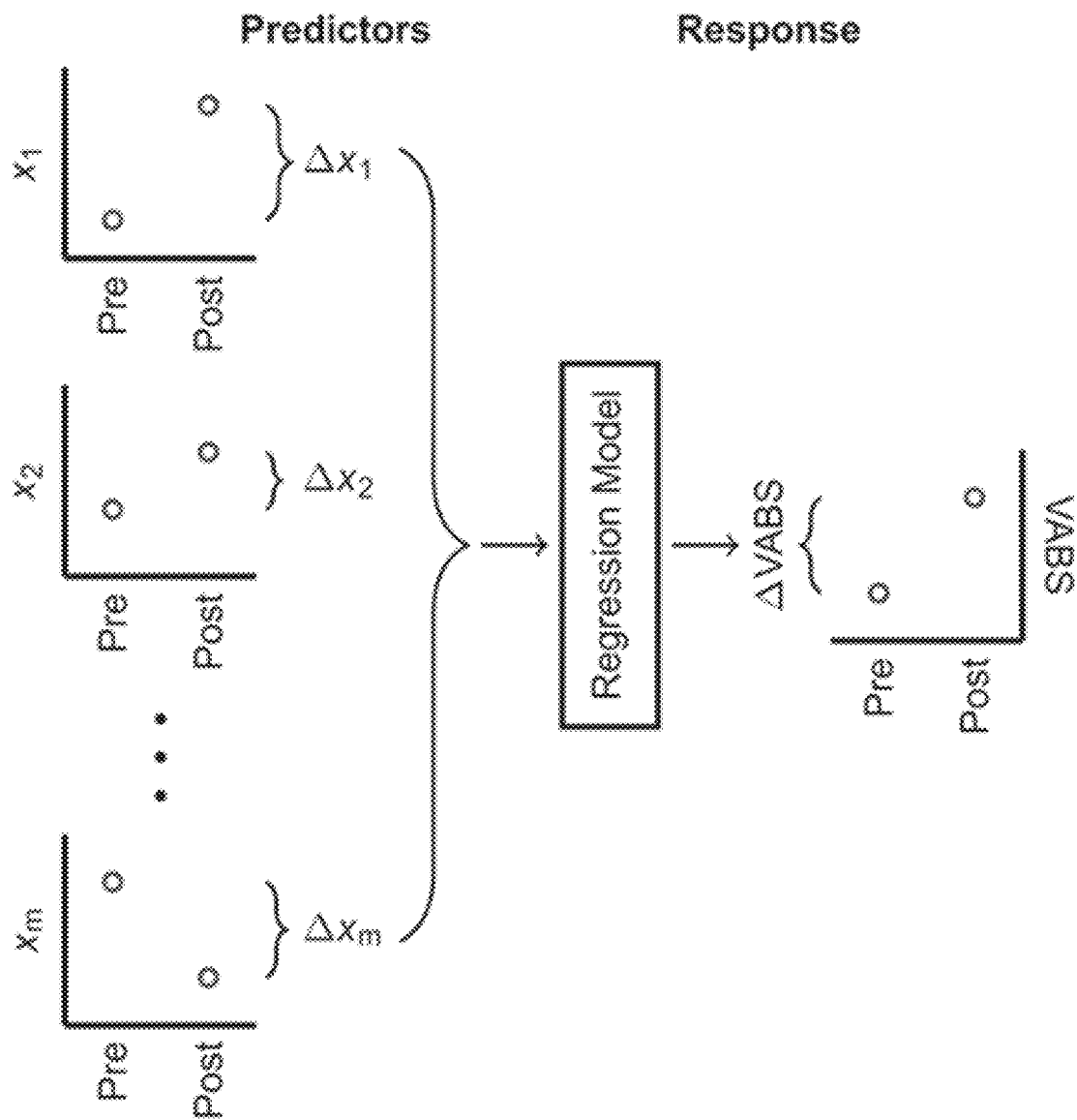
FIG. 3B is a graph of regression results for a regression model according to some embodiments of the present disclosure.

FDA Model Evaluation of Treatment Data. Using the FDA model identified from the IMAGE data and based on the same subset of FOCM/TS measurements, pre- and post-treatment discriminant scores were calculated for individuals with ASD who received the MeCbl+LDFA, BH$_4$, HDFA, and placebo treatments. Pre- and post-treatment Type II errors with respect to $H_0$, which was previously determined from model fitting involving data from the IMAGE study, were then computed for the estimated PDFs of pre- and post-treatment discriminant scores (separately for each treatment). Referring now to FIGS. 3A-3B, the change in Type II error yielded by each treatment was used to quantify the abilities of these treatments to shift the metabolic profiles of individuals with ASD to be more, or less, similar to those of the TD cohort. Without wishing to be bound by theory, an increase in Type II error, while undesirable in traditional hypothesis testing, is a desirable outcome in this particular analysis as the aim is to make the PDF of participants with ASD indistinguishable from the PDF of TD participants on the basis of their metabolic measurements.

Figure 4A:
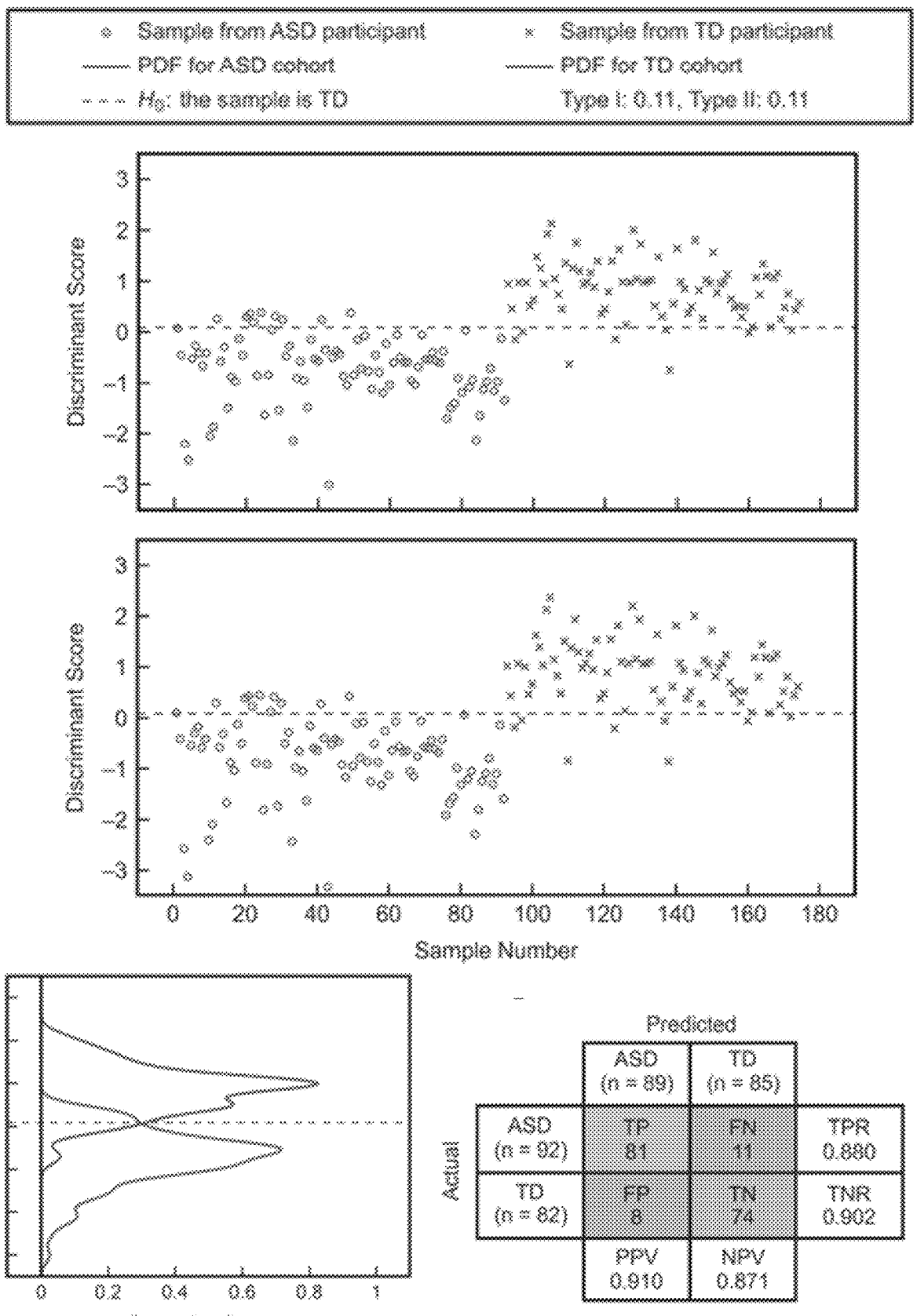
FIG. 4A portrays classification results for a Fisher Discriminant Analysis model according to some embodiments of the present disclosure.
Figure 4B:
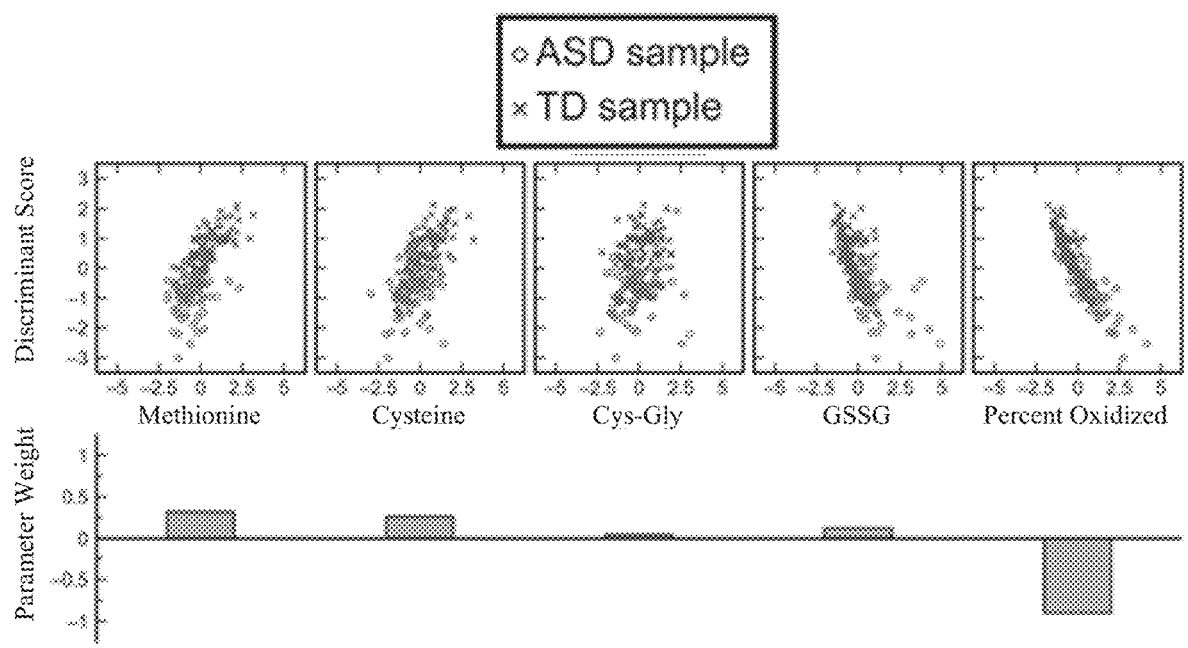
FIG. 4B portrays classification results for a Fisher Discriminant Analysis model according to some embodiments of the present disclosure.

FDA Model Identification from IMAGE Data. Referring now to FIGS. 4A-4B, a subset of five variables including methionine, cysteine, Cys-Gly, GSSG, and percent oxidized was selected then evaluated with FDA using cross-validation. This model predicted the left-out samples with a sensitivity of 88.0% and specificity of 90.2%, indicating very good classification accuracy. Investigation of each variable's contribution to the model's discriminant score revealed that the separation between the ASD and TD cohorts was largely determined by glutathione precursors and redox measurements (cysteine, Cys-Gly, GSSG, percent oxidized) with the methylation metabolites (methionine) having a considerably smaller effect on the classification. Individuals' measurements for percent oxidized glutathione, in particular, were highly correlated with the discriminant score output by the model.

To investigate individual variable contributions beyond the best model, the frequencies with which each of the fifteen measurements were used in five-variable models offering a fitted C-statistic of 0.96 or greater were considered (see FIG. 4B). This criterion was satisfied by 85 FDA models, out of a possible 3003 five-variable models overall, and it was found that the variables methionine, cysteine, and percent oxidized each appeared in more than 84% of these models while no other measurement was used in more than 32% of models. The measurement of percent oxidized, specifically, was used in almost 98% of the top models, reinforcing its importance for distinguishing participants in the ASD and TD cohorts.

Treatment Effect Sizes. The effect size for each treatment was calculated as the median pre-to-post-treatment change in discriminant score, with each participant's pre-treatment score paired with their post-treatment score. The distribution of the effect size was obtained by bootstrap resampling, i.e. random sampling, with replacement, for a sample set equal in size to the original set, with 10,000 replications, and the 0.025 and 0.975 quantiles of this bootstrap distribution described the 95% confidence interval for the effect size.

Figure 5:
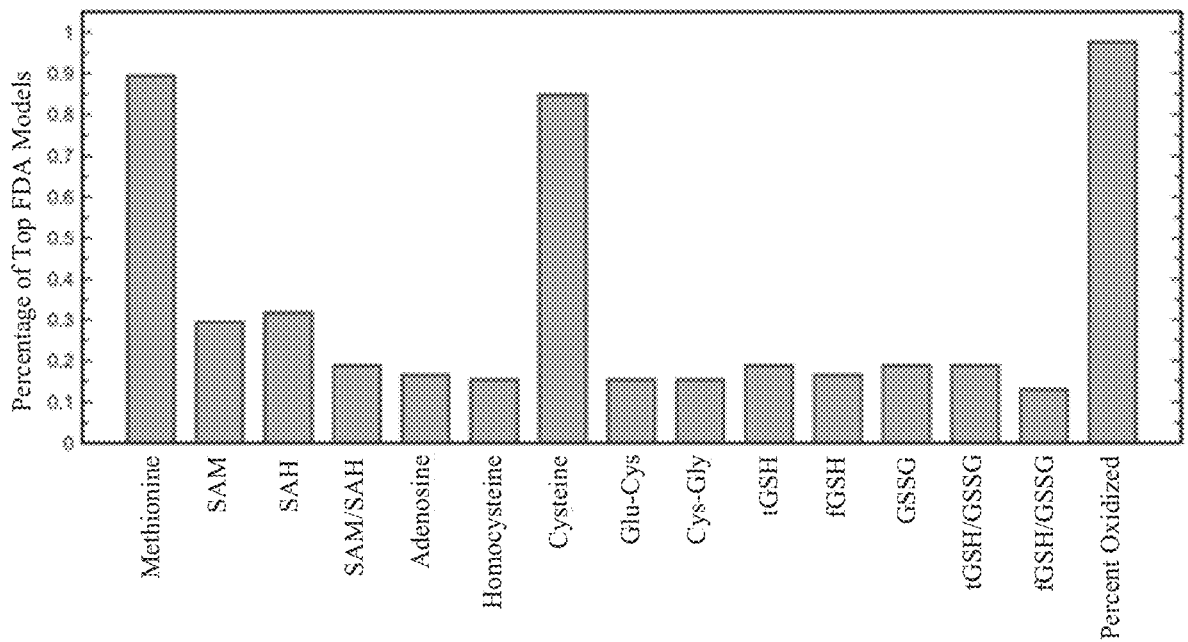
FIG. 5 is a graph portraying data concerning relative frequency of metabolites in exemplary models consistent with some embodiments of the present disclosure.

Treatment Effects on Overall Metabolic Status. Referring now to FIG. 5, to assess the efficacies of each clinical treatment (MeCbl+LDFA, $BH_4$, HDFA, and placebo) to correct metabolic abnormalities in individuals with ASD, pre- and post-treatment observations from the four groups were evaluated with the identified FDA model. PDFs of the resulting discriminant scores were estimated and compared to the ASD and TD distributions generated from the IMAGE data. Without wishing to be bound by theory, the treatments producing the largest pre-to-post-treatment shifts towards the TD distribution can be understood as those offering the greatest improvements to overall FOCM/TS metabolic status. As discussed above and referring to Table 2 below, these shifts were quantified as the change in Type II error associated with the PDFs, with respect to the null hypothesis $H_0$, brought about by each treatment. MeCbl+LDFA produced the largest increase in Type II error, followed by $BH_4$, indicating that these treatments were the most successful in altering the FOCM/TS profiles of individuals with ASD to more closely reflect those of TD individuals. Treatment with HDFA produced a relatively small increase in Type II error; however, due to the Type II error in this group being very large initially, the post-HDFA treatment error was actually the greatest among all treatments. As a result, the 95% CI for the effect size of HDFA contained zero whereas the 95% CIs for the other treatments did not contain zero. The 95% CI for the placebo unexpectedly did not contain zero, indicating a small, but statistically significant, metabolic shift in this group.

TABLE 2

Changes in Type II error associated with the PDFs of discriminant scores before and after each treatment, with respect to the null hypothesis $H_0$. Effect size was calculated as the median change in pre-to-post-treatment discriminant score, where pre-treatment samples were paired with their post-treatment data points.

| Treatment | Pre-treatment Type II Error | Post-treatment Type II Error | Change in Type II Error | Effect Size (95% CI) |
|---|---|---|---|---|
| MeCbl + LDFA | 1.7% | 43.6% | +41.9% | 0.89 (0.68, 1.40) |
| $BH_4$ | 0.3% | 41.1% | +40.8% | 0.73 (0.31, 1.11) |
| HDFA | 32.2% | 49.5% | +17.2% | 0.17 (−0.21, 0.46) |
| Placebo | 15.1% | 21.3% | +6.20% | 0.31 (0.12, 0.60) |

Regression. Kernel partial least squares (KPLS), a nonlinear extension of the partial least squares (PLS) algorithm, was used. KPLS regression handles noisy and collinear data well compared to ordinary least squares and is a more appropriate choice when the number of observations is small compared to the number of variables. The regression task began with the predictor variable set X (containing pre-to-post-treatment changes in FOCM/TS measurements) and the response variable set Y (containing pre-to-post-treatment changes in the VABS Composite). To initiate the PLS algorithm, a projection vector for the n samples contained in X is determined and a separate projection vector for the n samples contained in Y is identified. The projections of X and Y were then used to calculate the regression coefficients for the model. Further projection directions can be found by subtracting the contributions of the previous directions from X and Y.

KPLS regression first carried out a nonlinear transformation of the form $F=\Phi(X)$ on the predictor set, with the dimension of F typically much larger than that of X. The algorithm then proceeded in a modified form of linear PLS to identify the regression model for predicting Y from F, rather than from X. Gaussian kernel functions were used for the nonlinear transformation $\Phi(X)$. Here, X contained the pre-to-post-treatment changes of a subset of the measured metabolites and Y described the pre-to-post-treatment change in the VABS Composite. FIG. 3B provides a summary of these predictor and response variables used to develop the regression model.

Cross-Validation. Classification and regression analyses made use of leave-one-out cross-validation to provide a statistically independent assessment of model predictions. This technique removes one sample from the data set, identifies the FDA or KPLS model that fits the remaining data, and then uses the model to predict the sample that was removed. The sample is then replaced and the procedure repeated until all samples have been individually removed once. For classification, the confusion matrix is then constructed using the cross-validated predictions instead of the fitted discriminant scores. Similarly, the sum of squared errors for assessing a regression model was computed as the difference between the measured and the predicted, rather than the fitted, values. Approaching the modeling tasks in this manner helps to alleviate concerns of over-fitting that may arise during model development.

Prediction of Changes in Adaptive Behavior. Treatments with MeCbl+LDFA, $BH_4$, and HDFA offer varying levels of improvement in metabolic status in individuals with ASD. As discussed above, the predictor variables in the regression were the pre-to-post-treatment changes in metabolic measurements while the response variable was the pre-to-post-treatment change in VABS Composite. All treatment groups, including the placebo group, were included in the regression (74 samples in total) so as to capture a range of biochemical/behavioral effects and to further guard against overfitting by using metabolites from as many participants as possible. This analysis is independent of the treatment used as the changes in the pre-to-post-treatment are correlated with changes in the VABS scores and information about the treatment itself is not used for regression. Without wishing to be bound by theory, the type of treatment used affects the pre-to-post-treatment changes in the metabolites, but the treatment information is may be implicitly and not explicitly involved in this analysis.

All combinations of each number of variables were exhaustively tested and the $R^2$ from cross-validation was used as the evaluation criterion for the regression. Comparing the maximum $R^2$ given by each number of input variables showed the model performance to decrease when more than six variables were used. The highest cross-validated $R^2$ of 0.471 was obtained using $\Delta$methionine, $\Delta$Glu-Cys, $\Delta$Cys-Gly, $\Delta$tGSH, $\Delta$tGSH/GSSG, and $\Delta$fGSH/GSSG as predictor variables in the regression, where $\Delta$ indicates the pre-to-post-treatment change of a particular metabolite or metabolite ratio. The five top-performing models using six predictor variables are listed in Table 3 below.

TABLE 3

The five combinations of predictor variables producing the highest R2 from cross-validation with KPLS regression when using six variables.

| Variables | $R^2$ |
|---|---|
| $\Delta$Methionine, $\Delta$G1u-Cys, $\Delta$Cys-Gly, $\Delta$tGSH, $\Delta$tGSH/GSSG, $\Delta$fGSH/GSSG | 0.471 |
| $\Delta$Methionine, $\Delta$SAM/SAH, $\Delta$Adenosine, $\Delta$Cysteine, $\Delta$Cys-Gly, tGSH/GSSG | 0.470 |
| $\Delta$Methionine, $\Delta$SAM, $\Delta$SAM/SAH, $\Delta$Adenosine, $\Delta$Cysteine, $\Delta$Cys-Gly | 0.467 |
| $\Delta$SAM, $\Delta$SAM/SAH, $\Delta$Homocysteine, $\Delta$Cysteine, $\Delta$Cys-Gly, $\Delta$tGSH/GSSG | 0.462 |
| $\Delta$Methionine, $\Delta$SAM/SAH, $\Delta$Adenosine, $\Delta$Cys-Gly, $\Delta$tGSH/GSSG, $\Delta$fGSH/GSSG | 0.454 |

Methods and systems of the present disclosure enable classification of ASD and TD individuals, as well as prediction of improvements in adaptive behavior in ASD individuals, based on metabolic data. Classification of ASD and TD individuals showed very good separation between these groups with a classifier sensitivity of 88.0% and specificity of 90.2%. The methods and systems of the present disclosure go beyond univariate comparisons of individual measurements, and instead consider the combined contributions of multiple markers towards FOCM/TS metabolic status. Including participants receiving the placebo substantially increases the number of samples for model training and cross-validation and provides further safeguard against overfitting. The use of regression of changes in adaptive behavior and changes in biochemical measurements offers insight into the metabolic and behavioral improvements resulting from clinical treatment of individuals with ASD and allow care providers to monitor and adjust treatment of these individuals accordingly.

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

What is claimed is:

1. A method to predict changes in adaptive behavior comprising:
    performing a multivariate statistical analysis on one or more data sets of typically developing (TD) individuals and one or more data sets of autism spectrum disorder (ASD) individuals to produce a model that classifies TD individuals from ASD individuals, wherein the TD data sets include metabolic profile data for a plurality of TD individuals and ASD data sets include pre-treatment metabolic profile data and post-treatment metabolic profile data for patients receiving one or more ASD treatments;
    calculating pre-treatment discriminant scores and post-treatment discriminant scores for a plurality of patients in the ASD data sets;
    identifying a change from the pre-treatment discriminant score to the post-treatment discriminant score to quantify a positive treatment effect by at least one of the ASD treatments on metabolic profiles of the plurality of patients;
    administering a particular ASD treatment associated with a quantified positive treatment effect to a target patient;
    performing a treatment effect regression analysis on changes in adaptive behavior scores and metabolic profiles of the plurality of patients; and
    quantifying a predicted adaptive behavior score change for the target patient from a measured metabolic profile change in the target patient,
    wherein the particular ASD treatment includes MeCbl+ LDFA, $BH_4$, HDFA, or combinations thereof.

2. The method according to claim 1, wherein the metabolic profile data includes data for folate-dependent one-carbon metabolism (FOCM) metabolites, transsulfuration (TS) pathway metabolites, methionine, SAM, SAH, SAM/SAH, 8-OHG, adenosine, homocysteine, cysteine, γ-L-glutamyl-L-cysteine (Glu.-Cys.), L-cysteine-L-glycine (Cys.-Gly.), tGSH, fGSH, GSSG, fGSH/GSSG, tGSH/GSSG, chlorotyrosine, nitrotyrosine, tyrosine, tryptophane, fCystine, fCysteine, fCystine/fCysteine, a percent of DNA methylation, a percent of oxidized glutathione, or combinations thereof.

3. The method according to claim 1, wherein the multivariate statistical analysis comprises performing a Fisher discriminant analysis.

4. The method according to claim 1, wherein the one or more ASD treatments include placebo treatments.

5. The method according to claim 1, wherein the adaptive behavior score includes a Vineland Adaptive Behavior Scales (VABS) Composite score.

6. The method according to claim 1, wherein the treatment effect regression analysis includes use of a kernel partial least squares algorithm.

7. The method according to claim 6, wherein identifying a change from the pre-treatment discriminant score to the post-treatment discriminant score to quantify a positive treatment effect by at least one of the ASD treatments on metabolic profiles of the plurality of patients includes:
    calculating, for the plurality of patients in the ASD data sets, a first probability that the model will classify a data set patient as TD pre-treatment and a second probability that the model will classify the data set patient as TD post-treatment; and identifying an increase from the first probability to the second probability.

8. A method to predict changes in adaptive behavior comprising:

performing Fisher discriminant analysis on one or more data sets of typically developing (TD) individuals and one or more data sets of autism spectrum disorder (ASD) individuals to produce a model that classifies TD individuals from ASD individuals, wherein the TD data sets include folate-dependent one-carbon metabolism (FOCM) and transsulfuration (TS) pathway metabolic profile data for a plurality of TD individuals and ASD data sets include pre-treatment folate-dependent one-carbon metabolism (FOCM) and transsulfuration (TS) pathway metabolic profile data and post-treatment folate-dependent one-carbon metabolism (FOCM) and transsulfuration (TS) pathway metabolic profile data for patients receiving one or more ASD treatments;

calculating, for the plurality of patients in the ASD data sets, a first probability that the model will classify a data set patient as TD pre-treatment and a second probability that the model will classify the data set patient as TD post-treatment;

identifying an increase from the first probability to the second probability to quantify a positive treatment effect by at least one of the ASD treatments on metabolic profiles of the plurality of patients;

administering a particular ASD treatment associated with a quantified positive treatment effect to a target patient;

performing a treatment effect regression analysis on changes in adaptive behavior scores and metabolic profiles of the plurality of patients; and quantifying a predicted adaptive behavior score change for the target patient from a measured metabolic profile change in the target patient, wherein the particular ASD treatment includes MeCbl+LDFA, $BH_4$, HDFA, or combinations thereof.

9. The method according to claim 8, wherein the treatment effect regression analysis includes use of a kernel partial least squares algorithm.

* * * * *